United States Patent [19]

Yankee

[11] 4,160,106

[45] Jul. 3, 1979

[54] ω-ARYL-CIS-13-INTER-OXA-PGF COMPOUNDS

[75] Inventor: Ernest W. Yankee, Portage, Mich.

[73] Assignee: The Upjohn Company, Kalamazoo, Mich.

[21] Appl. No.: 904,186

[22] Filed: May 8, 1978

Related U.S. Application Data

[62] Division of Ser. No. 774,186, Mar. 3, 1977, which is a division of Ser. No. 595,869, Jul. 14, 1975, Pat. No. 4,026,909.

[51] Int. Cl.$^2$ .............................................. C07C 177/00
[52] U.S. Cl. ..................................... 560/55; 562/471; 562/465
[58] Field of Search ................... 560/55; 562/465, 471

[56] References Cited

PUBLICATIONS

Derwent Abstract, 84516v/49, BE 815-355, 11/21/74.
Derwent Abstract, 84515v/49, BE 815-354, 11/21/74.

*Primary Examiner*—Paul J. Killos
*Attorney, Agent, or Firm*—Robert A. Armitage

[57] ABSTRACT

This invention comprises certain analogs of the prostaglandins in which the double bond between C-13 and C-14 is of the cis configuration. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

37 Claims, No Drawings

ω-ARYL-CIS-13-INTER-OXA-PGF COMPOUNDS

The present application is a divisional application of Ser. No. 774,186, filed Mar. 3, 1977; which is a divisional application of Ser. No. 595,869, filed July 14, 1975, now issued as U.S. Pat. No. 4,026,909 on May 31, 1977.

The present invention relates to prostaglandin analogs for which the essential material constituting disclosure therefor is incorporated by reference here from Ser. No. 595,869, filed July 14, 1975, now issued as U.S. Pat. No. 4,026,909.

I claim:

1. A prostaglandin analog of the formula:

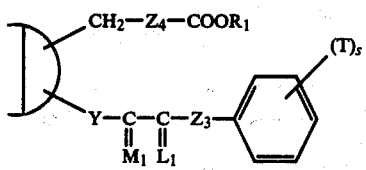

wherein D is

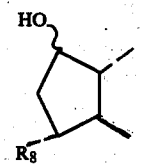

or

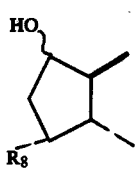

wherein $R_8$ is hydrogen or hydroxy;
wherein Y is cis—CH=CH—;
wherein $Z_4$ is
 (1) —$CH_2$—O—$CH_2$—$(CH_2)_g$—$CH_2$—,
 (2) —$(CH_2)_2$—O—$(CH_2)_g$—$CH_2$—, or
 (3) —$(CH_2)_3$—O—$(CH_2)_g$—,
wherein g is one, 2, or 3;
wherein $Z_3$ is oxa or methylene;
wherein T is chloro, fluoro, trifluoromethyl. alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl;
wherein $M_1$ is

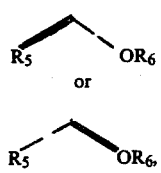

wherein $R_5$ and $R_6$ are hydrogen or methyl, with the proviso that one of $R_5$ and $R_6$ is methyl only when the other is hydrogen;

wherein $L_1$ is

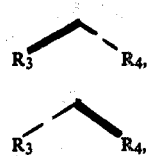

or a mixture of

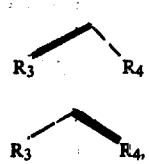

wherein $R_3$ and $R_4$ are hydrogen, methyl, or fluoro, being the same or different, with the proviso that one of $R_3$ and $R_4$ is fluoro only when the other hydrogen or fluoro and $Z_3$ is methylene; and
wherein $R_1$ is hydrogen, alkyl of one to 12 carbon atoms, inclusive, cycloalkyl of 3 to 10 carbon atoms, inclusive, aralkyl of to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein D is

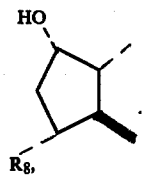

3. A compound according to claim 1, wherein D is

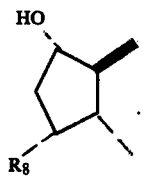

4. A compound according to claim 3, wherein $Z_3$ is methylene.

5. A compound according to claim 4, wherein s is zero or one and T is chloro, fluoro, or trifluoromethyl.

6. A compound according to claim 3, wherein $Z_3$ is oxa.

7. A compound according to claim 6, wherein s is zero.

8. A compound according to claim 6, wherein s is zero or one and T is chloro, fluoro, or trifluoromethyl.

9. A compound according to claim 8, wherein $Z_4$ is —$(CH_2)_3$—O—$(CH_2)_g$—.

10. A compound according to claim 8, wherein $Z_4$ is —$(CH_2)_2$—O—$(CH_2)_g$—$CH_2$—.

11. A compound according to claim 8, wherein $Z_4$ is —$CH_2$—O—$CH_2$—$(CH_2)_g$—$CH_2$—.

12. A compound according to claim 11, wherein $M_1$ is

13. A compound according to claim 12, wherein g is one.

14. A compound according to claim 13, wherein $R_3$, $R_4$, $R_5$, and $R_6$ are all hydrogen.

15. 15-epi-5-oxa-16-phenoxy-17,18,19,20-tetranor-cis-13-$PGF_{1\alpha}$, methyl ester, a compound according to claim 14.

16. A compound according to claim 11, wherein $M_1$ is

17. A compound according to claim 16, wherein g is three.

18. A compound according to claim 16, wherein g is one.

19. A compound according to claim 18, wherein $R_3$ and $R_4$ are both hydrogen.

20. A compound according to claim 19, wherein $R_5$ is methyl.

21. 5-Oxa-16-phenoxy-17,18,19,20-tetranor-15-methyl-cis-13-$PGF_{1\alpha}$, a compound according to claim 20.

22. 5-Oxa-16-phenoxy-17,18,19,20-tetranor-15-methyl-cis-13-$PGF_{1\alpha}$, methyl ester, a compound according to claim 20.

23. A compound according to claim 19, wherein $R_6$ is methyl.

24. 5-Oxa-16-phenoxy-17,18,19,20-tetranor-cis-13-$PGF_{1\alpha}$, 15-methyl ether, a compound according to claim 23.

25. 5-Oxa-16-phenoxy-17,18,19,20-tetranor-cis-13-$PGF_{1\alpha}$, methyl ester, 15-methyl ether, a compound according to claim 23.

26. A compound according to claim 19, wherein $R_5$ and $R_6$ are both hydrogen.

27. 5-Oxa-16-phenoxy-17,18,19,20-tetranor-cis-13-$PGF_{1\alpha}$, a compound according to claim 26.

28. 5-Oxa-16-phenoxy-17,18,19,20-tetranor-cos-13-$PGF_{1\alpha}$, methyl ester, a compound according to claim 26.

29. A compound according to claim 18, wherein at least one of $R_3$ and $R_4$ is methyl.

30. A compound according to claim 29, wherein $R_3$ and $R_4$ are both methyl.

31. A compound according to claim 30, wherein $R_5$ is methyl.

32. 5-Oxa-16-phenoxy-18,19,20-trinor-14,15-dimethyl-cis-13-$PGF_{1\alpha}$, methyl ester, a compound according to claim 31.

33. A compound according to claim 30, wherein $R_6$ is methyl.

34. 5-Oxa-16-phenoxy-18,19,20-trinor-16-methyl-cis-13-$PGF_{1\alpha}$, methyl ester, 15-methyl ether, a compound according to claim 33.

35. A compound according to claim 30, wherein $R_5$ and $R_6$ are both hydrogen.

36. 5-Oxa-16-phenoxy-18,19,20-trinor-16-methyl-cis-13-$PGF_{1\alpha}$, a compound according to claim 35.

37. 5-Oxa-16-phenoxy-18,19,20-trinor-16-methyl-cis-13-$PGF_{1\alpha}$, methyl ester, a compound according to claim 35.

* * * * *

UNITED STATES PATENT OFFICE
CERTIFICATE OF CORRECTION

Patent No. 4,160,106                    Dated   3 July 1979

Inventor(s)   Ernest W. Yankee

It is certified that error appears in the above-identified patent and that said Letters Patent are hereby corrected as shown below:

Column 2, line 21, "other hydrogen" should read -- other is hydrogen --; line 25, "aralkyl of to 12" should read -- aralkyl of 7 to 12 --;

Column 4, line 20-21, "14,15-dimethyl-" should read -- 15,16-dimethyl- --.

Signed and Sealed this

Twentieth Day of November 1979

[SEAL]

Attest:

RUTH C. MASON
Attesting Officer

LUTRELLE F. PARKER
Acting Commissioner of Patents and Trademarks